United States Patent [19]

Gohlke et al.

[11] 4,378,458

[45] Mar. 29, 1983

[54] NOVEL CHROMOGENIC AND/OR FLUOROGENIC SUBSTRATES FOR MONITORING CATALYTIC OR ENZYMATIC ACTIVITY

[75] Inventors: James R. Gohlke, Yorktown Heights; Eddie Hedaya, Hartsdale; Jemo Kang, Mt. Kisco, all of N.Y.; Jeanette D. Mier, South Charleston, W. Va.

[73] Assignee: Baker Instruments Corporation, Bethlehem, Pa.

[21] Appl. No.: 248,672

[22] Filed: Mar. 30, 1981

[51] Int. Cl.$^3$ .................... C07H 19/10; C07H 19/20
[52] U.S. Cl. .................................... 536/29; 536/27; 536/28
[58] Field of Search .................... 536/27, 28, 29, 4

[56] References Cited

U.S. PATENT DOCUMENTS

| | | |
|---|---|---|
| 3,817,837 | 6/1974 | Rubenstein et al. |
| 3,852,157 | 12/1974 | Rubenstein et al. |
| 3,875,011 | 4/1975 | Rubenstein et al. |
| 3,905,871 | 9/1975 | Rubenstein et al. |
| 3,966,556 | 6/1976 | Rubenstein et al. |
| 3,996,345 | 12/1976 | Ullman et al. |
| 3,998,943 | 12/1976 | Ullman |
| 4,039,385 | 8/1977 | Ullman et al. |
| 4,040,907 | 8/1977 | Ullman et al. |
| 4,043,872 | 8/1977 | Blakemore et al. |
| 4,046,636 | 9/1977 | Ullman et al. |
| 4,065,354 | 12/1977 | Ullman et al. |
| 4,067,774 | 1/1978 | Rubenstein et al. |
| 4,160,016 | 7/1979 | Ullman |
| 4,161,515 | 7/1979 | Ullman |
| 4,171,244 | 10/1979 | Blakemore et al. |
| 4,174,384 | 11/1979 | Ullman et al. |
| 4,191,613 | 3/1980 | Rubenstein et al. |
| 4,208,479 | 6/1980 | Zuk et al. |

FOREIGN PATENT DOCUMENTS 81969  8/1976  Poland.

OTHER PUBLICATIONS

J. F. Burd, R. C. Wong, J. E. Feeney, R. J. Carrico and R. C. Boguslaski, *Clin. Chem.*, 23, (1977) 1402.
Burd, Carrico, M. L. Fetter, et al., *Anal. Biochem.*, 77, (1977), 56.
F. Kohen, Z. Hollander and Boguslaski, *Jour. of Steroid Biochem.*, 11, (1979) 161.
F. M. Richards and H. W. Wyckoff, *The Enzymes*, (P. D. Boyer, Ed.), Academic Press, 3d Edition, vol. 4, (1978), 647-806, London and New York (See also p. 14).
M. Kunitz, *J. Biol. Chem.*, 164, (1946), 563.
C. B. Anfinsen, R. R. Redfield, W. L. Choate, A. Page and W. R. Carroll, *Jour. Biol. Chem.*, 207, (1954) 201.
R. C. Kamm, A. G. Smith and H. Lyons, *Analyt. Biochem.*, 37, (1970), 333.
E. M. Crook, A. P. Mathias and B. R. Rabin, *Biochem J.*, 74, (1960), 234.
H. Sierakowska, M. Zan-Kowalczewska and D. Shugar, *Biochem. Biophys. Res. Comm.*, 19, (1965) 138.
M. Zan-Kowalczewska, A. Sierakowska and D. Shugar, *Acta. Biochem. Polon.*, 13, (1966), 237.
H. Sierakowska and D. Shugar, *Acta Biochem. Polon.*, 18, (1971), 143.
H. Sierakowska and D. Shugar, *Biochem. Biophys. Res. Comm.*, 11, (1963) 70.
R. Kole and H. Sierakowska, *Acta. Biochem. Polon.*, 18, (1971) 187.
H. Rubsamen, R. Khandler and H. Witzel, *Hoppe-Seyler's Z. Physiol. Chem.*, 355, (1974), 687.
S. Levit and M. S. Joshi, *Analytical Biochemistry*, 84, (1978), 343-345.
A. Holy and F. Sorm, *Biochemica. Biophsica. Acta.*, 161, (1968), 264.
A. Weller, *Prog. in Reaction Kinetica*, 1, (1961), 189.
R. Kole, H. Sierakowska, and D. Shugar, *Biochem. Biophys. Acta.*, 289, (1972) 323.

Primary Examiner—Blondel Hazel

[57] ABSTRACT

Novel substrates for monitoring of catalytic activity resulting in hydrolytic release of products which can be readily detected by spectrophotometric or fluorometric means are provided. The substrates have the general formula:

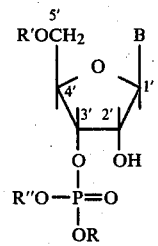

wherein B is a nucleotide base capable of assisting in hydrolysis of the phosphate ester at the 3'-position; R is a moiety selected from the group consisting of umbelliferonyl, 4-methylumbelliferonyl, 3-flavonyl, o-nitrophenyl, m-nitrophenyl, p-nitrophenyl, dinitrophenyl, cyanophenyl, acylphenyl, carboxyphenyl, phenylsulfonate, phenylsulfonyl and phenylsulfoxide; R' is a moiety selected from the group consisting of hydrogen, alkyl, alkenyl cycloalkyl, aryl, araalkyl, acyl, oxaalkyl, thioalkyl, oxacycloalkyl, and thiocycloalkyl and R'' is hydrogen or a cation selected from the group consisting of calcium, barium, lithium, sodium, ammonium, substituted ammonium and pyridinium. The substrates are capable of undergoing catalytic-induced hydrolysis of the phosphate ester at the 3'-position to yield a species capable of being monitored spectrophotometrically or fluorometrically.

15 Claims, No Drawings

NOVEL CHROMOGENIC AND/OR FLUOROGENIC SUBSTRATES FOR MONITORING CATALYTIC OR ENZYMATIC ACTIVITY

RELATED APPLICATIONS

Farina and Gohlke, Ser. No. 248,689 filed Mar. 30, 1981, for A Method for Carrying Out Non-Isotopic Immunoassays, Labeled Analytes and Kits for Use in Such Assays.

Kang & Tolman, Ser. No. 248,682 filed Mar. 30, 1981, for A Method for Making Chromogenic and/or Fluorogenic Substrates for Use in Monitoring Catalytic or Enzymatic Activity.

Kang, Ser. No. 248,688 filed Mar. 30, 1981, for A Method for Making Chromogenic and/or Fluorogenic Substrates for Use in Monitoring Catalytic or Enzymatic Activity.

BACKGROUND OF THE INVENTION

1. Field of the Invention

The present invention relates to novel compounds, and more particularly to novel assay reagents suitable for use, inter alia, in the detection and measurement of catalytic activity from an enzyme or polypeptide pair, natural or synthetic, having the catalytic activity of an enzyme in the analysis of various compounds in biological fluids or the like.

2. Description of the Prior Art

For a variety of clinical purposes such as, for example, monitoring dosage schedules, monitoring hormone levels, checking for recent ingestion or following pharmacological dynamics of bioavailability, absorption, degradation or excretion, it is a great advantage to measure the concentration of various drugs or the like to the nanomolar or even picomolar level. As is known, radioimmunoassay can accomplish analyses of this type. To carry out an analysis, an acceptable kit or system must include an antiserum, a standard or known concentrations of the compound (i.e.,—analyte) to be measured, a radiolabeled derivative of the compound to be measured, and a buffering agent or agents. The antiserum is produced by bleeding animals which have been immunized by innoculation, for example, with the hapten-protein conjugate (immunogen) corresponding to the compound to be measured.

As is well known, the technique of radioimmunoassay, in general, measures the competition between radioactively labeled analyte and unlabeled analyte for binding sites on the antibody in the antiserum. By adding to the antiserum known amounts of the analytes to be assayed and a radiolabeled analog, a dose-response curve for bound or free analyte versus concentration of analyte is constructed. After this immuno-calibration has been carried out, unknown concentrations can then be compared to the standard dose-response curve for assay. Crucial to this type of assay is the existence of radioactive analytes which compete effectively with non-radioactive analytes. Accordingly, in order to obtain the maximum precision, accuracy, sensitivity, specificity and reproducibility of the assay, purified, well-characterized synthetic radioactive analytes are required.

Several deficiencies in radioimmunoassay methodology have been identified. First of all, it is necessary to make a physical separation of the antibody bound radiolabeled analyte from the free radiolabeled analyte. Further, the methodology is considered rather labor intensive; and the equipment required is likewise relatively expensive, is not uniformly available, and further requires the use of highly trained and skilled technicians to accurately carry out such assays. Likewise, the radioisotopically-labeled analytes are relatively unstable and expensive and pose an increasingly severe waste disposal problem owing to radiation exposure hazards associated with the commonly used radioisotopic labels. Despite these shortcomings, the use of radioimmunoassay has grown considerably.

The substantial recent growth in the use of radioimmunoassay in clinical laboratories has, however, spurred the development of variants which overcome the deficiencies of the radioimmunoassay methodology as described herein. The approaches which have been developed to overcome these deficiencies primarily involve the use of enzyme or fluorescent labels instead of radioisotopic labels, preferably coupled with conditions allowing for measuring a chemical distinction between bound and free fractions of labeled analyte which leads to the elimination of the requirement for physical separation. Immunoassays having the latter simplifying and advantageous feature are referred to as homogeneous immunoassays as opposed to heterogeneous immunoassays where physical separation is required.

Thus, homogeneous immunoassay systems have been developed which are based on the use of an enzyme-labeled analyte where the enzymatic activity of the label is decreased when complexation with the antibody occurs. Unlabeled analyte whose concentration is to be determined displaces the enzyme-labeled analyte bound to the antibody, thus causing an increase in enzymatic activity. Standard displacement or dose-response curves are constructed where increased enzymatic activity (monitored spectophotometrically using what has been termed a "substrate" which ultimately produces a unique chromophore as a consequence of enzyme action) is plotted against increased analyte concentration. These are then used for determining unknown concentrations. The following U.S. patents have been issued in the field of homogeneous enzyme immunoassay: U.S. Pat. Nos. 3,817,837; 3,852,157; 3,875,011; 3,966,556; 3,905,871; 4,065,354; 4,043,872; 4,040,907; 4,039,385; 4,046,636; 4,067,774; 4,191,613; and 4,171,244. In these patents, the label for the analyte is described as an enzyme having a molecular weight substantially greater than 5,000. Commercialization of this technology has been limited so far to applications where the analytes are relatively small in molecular size at fluid concentrations of the analyte greater than $10^{-10}$ M.

As a consequence of the limitations of the homogeneous enzyme immunoassay techniques described above, considerable effort has been devoted towards developing more sensitive homogeneous immunoassays using fluorescence. These have been primarily directed at assays for the larger sized molecules such as immunoglobulins or polypeptide hormones such as insulin. The following U.S. patents have been issued for this type of assay: U.S. Pat. Nos. 3,998,943; 3,996,345; 4,174,384; 4,161,515; 4,208,479 and 4,160,016. The label in most of these patents involves an aromatic fluorescent molecule, bound either to the analyte or to the antibody. All likewise involve various methods of quenching fluorescence through antibodies or other fluorescent quenchers so that the extent of quenching is related to the amount of analyte present in the sample.

A further type of methodology which may be described as a reactant-labeled fluorescent immunoassay involves the use of a fluorescent-labeled analyte designed so that a fluorescent product is released when it is enzymatically hydrolyzed. Antibody to the analyte portion of the molecule, however, inhibits enzymatic hydrolysis. Consequently, by the law of mass action, fluorescence is enhanced in the presence of increased analyte due to enzymatic hydrolysis of the displaced, fluorescent labeled analyte. As an example, a labeled analyte is $\beta$-galactosyl-umbelliferone-sisomicin. The enzyme $\beta$-galactosidase cleaves the sugar from the umbelliferone moiety which can then fluoresce. Publications which describe this methodology include: J. F. Burd, R. C. Wong, J. E. Feeney, R. J. Carrico and R. C. Boguolaski, *Clin. Chem.*, 23, 1402 (1977); Burd, Carrico, M. C. Fetter, et al., *Anal. Biochem.*, 77, 56 (1977) and F. Kohen, Z. Hollander and Boguolaski, *Jour. of Steroid Biochem.*, 11, 161 (1979).

Ribonucleases are a class of widely distributed and commonly known phosphodiesterases which specifically catalyze the hydrolysis of 3'-internucleotide phosphate ester bonds of ribonucleic acids, commonly known as RNA, but not those of deoxyribonucleic acids, commonly known as DNA, or the phosphate ester bonds of simple phosphodiesters, such as, for example, bis(p-nitrophenyl) phosphate. The study of the mechanism of the hydrolysis of ribonucleic acid has been extensively recorded in the literature. See the review by F. M. Richards and H. W. Wyckoff in *The Enzymes*, (P. D. Boyer, Ed.), Academic Press, 3d Edition, Volume 4, pages 647–806, London and New York (1978).

Many organic compounds have been utilized heretofore for monitoring the catalytic activity of ribonuclease. Such organic compounds, or substrates, as they are commonly referred to, include ribonucleic acid itself, cyclic phosphate diesters, and monoribonucleotide compounds which exhibit the same or similar structural constraints as those expressed by the natural substrate.

Thus, for example, one method for monitoring the catalytic activity of ribonclease involves the use of a ribonucleic acid solution. That method involves monitoring a decrease in absorbance at 300 nm of a ribonucleic acid solution as a function of time, M. Kunitz, *J. Biol. Chem.*, 164, 563 (1946). Although that method is relatively simple to conduct, it has several deficiencies; specifically, the rate of decrease of absorption is not linear, calibration of each substate solution is required, and direct monitoring of absorbance decreases at 300 nm is impractical with clinical samples.

Another method utilized for monitoring ribonuclease activity is an end-point variant of the procedure described above. In the end point variant procedure, yeast ribonucleic acid is incubated with the enzyme sample for a fixed period of time. The remaining RNA is precipitated with perchloric acid or uranyl acetate/trifluoroacetic acid, and the absorbance of the supernatant is measured after centrifugation, S. B. Anfinsen, R. R. Redfield, W. L. Choate, A. Page, and W. R. Carroll, *Jour. Biol. Chem.*, 207, 201 (1954). However, that method is much too cumbersome for homogeneous immunoassays of the type described in the co-pending Farina et al. application primarily due to the precipitation step involved.

Yet another variation of the above procedures has been reported by R. C. Kamm, A. G. Smith, and H. Lyons, *Analyt. Biochem.*, 37, 333 (1970). The method described therein is based on the formation of a fluorescent reaction product resulting from the reaction of the dye, ethidium bromide, with intact yeast ribonucleic acid, but not with the hydrolysis products. In that method, a fluorescent signal, which is monitored, decreases with time. However, monitoring a fluorescent signal which decreases with time is disadvantageous, as the method may result in a lack of sensitivity when only modest differences in enzyme concentration are encountered. In addition, other disadvantages are that the rate of decrease of absorption is not linear; and calibration of each substrate solution is required.

Another known substrate for monitoring ribonuclease activity is a mononucleotide substrate, cytidine 2', 3'-phosphate, E. M. Crook, A. P. Mathias, and B. R. Rabin, *Biochem. J.*, 74, 234 (1960). In that method, an increase of absorbance at 286 nm, corresponding to the hydrolysis of the cyclic phosphate ring, is monitored over a two-hour period to measure the ribonuclease activity of the sample. This method, however, cannot be used in homogeneous immunoassay methods of the type described in the Farina et al. co-pending application because there are analyte sample interferences which occur at 286 nm. Furthermore, the distinction between the substrate and product absorbance spectra is small, with the ratio of extinction coefficients being only 1.495 at 286 nm.

Further, certain mononucleotide-3'-phosphodiesters, including, 1-naphthyl esters of 3'-uridylic, 3'-inosinic and 3'-adenylic acids have been utilized as ribonuclease substrates. These naphthyl esters have been used to differentiate substrate specificities of ribonucleases from various sources. H. Sierakowska, M. Zan-Kowalczewska, and D. Shugar, *Biochem. Biophys. Res. Comm.*, 19, 138 (1965); M. Zan-Kowalczewska, A. Sierakowska, and D. Shugar, *Acta. Biochem. Polon.*, 13, 237 (1966); H. Sierakowska and D. Shugar, *Acta. Biochem. Polon.*, 18, 143 (1971); H. Sierakowska and D. Shugar, *Biochem. Biophys. Res. Comm.* 11, 70 (1963). As a result of ribonuclease-induced hydrolysis, the use of such substances results in the liberation of 1-naphthol which is allowed to react with a diazonium salt to form an azo compound having strong visible absorbance. This approach requires that the assay kit include a separately packaged dye forming reagent (viz.—a diazonium salt). Methods for preparing mononucleotide-3'-phosphodiesters are known. Syntheses are disclosed in R. Kole and H. Sierakowska, *Acta. Biochem. Polon,* 18, 187 (1971) and Polish Pat. No. 81969.

Still other compounds have been utilized for kinetically monitoring ribonuclease activities. Such compounds include 3'-uridylic acid phosphodiesters of 1-naphthol, 5-hydroxynaphthol, and 4-methoxyphenol, H. Rubsamen, R. Khandler, and H. Witzel, Hoppe-Seyler's *Z. Physiol. Chem.*, 355, 687 (1974). However, the hydrolysis product is monitored directly in the ultraviolet region, at or around 280 nm, where serum interferences are expected to occur. Further, these substrates are difficult to prepare, requiring numerous steps, including lengthy chromatographic procedures.

Thus, despite the considerable number of compounds that have been developed and utilized for monitoring ribonuclease activity, there remains the need for further development which can overcome the various shortcomings of the presently known substrates.

It is, accordingly, an object of the present invention to provide novel substrates which include species that may be utilized for both direct spectrophotometric and fluorometric monitoring of catalytic activity resulting from hydrolysis of the substrate.

A further object lies in the provision of a novel substrate which is catalytically converted to product rapidly enough so that the appearance of product can be monitored kinetically over a relatively short period of time.

A still further object of this invention is to provide a novel substrate which is sensitive to ribonuclease activity even at extremely low concentrations. A related object provides a substrate capable of readily allowing detection of ribonuclease activity at low concentrations in a variety of physiological fluids such as serum, urine and the like.

Yet another object of the present invention is to provide a substrate that may be readily prepared.

A still further object provides a substrate capable of being stored in a blocked form with long term hydrolytic stability. A related object lies in providing a blocked substrate which may be readily deblocked.

A further object of the present invention is to provide a substrate which may be employed in carrying out immunoassays. A related object provides a substrate capable of use in homogeneous immunoassays.

Another object provides a substrate which may be used in carrying out homogeneous immunoassays in centrifugal fast analyzers.

These and other objects and advantages of the present invention will become apparent from the following detailed description.

While the invention is susceptible to various modifications and alternative forms, there will herein be described in detail and preferred embodiments. It is to be understood, however, that it is not intended to limit the invention to the specific forms disclosed. On the contrary, it is intended to cover all modifications and alternative forms falling within the spirit and scope of the invention as expressed in the appended claims. For example, while the use of the substrate will be principally described in connection with immunoassays, it should be appreciated that the substrate may be employed for monitoring any system having a component or components capable of hydrolyzing the substrate. Thus, the substrate may be utilized to quantitatively detect the presence of ribonuclease or peptidase. (S. Levit and M. S. Joshi, *Analytical Biochemistry*, Vol. 84, pp. 343-345, 1978.)

SUMMARY OF THE INVENTION

The present invention concerns novel substrates for monitoring of catalytic activity resulting in hydrolytic release of products which can be readily detected by spectrophotometric or fluorometric means. The substrates are especially useful in the immunoassay methodology described in the co-pending Farina et al. application.

DETAILED DESCRIPTION OF THE SPECIFIC EMBODIMENTS

The novel substrates of the present invention find particular utility in the immunoassay methodology described in the co-pending Farina et al. application wherein analyte labeled with one partner of a polypeptide pair, antibody and polypeptide partner are present together in the sample being analyzed. The polypeptide labeled analyte is capable of binding, in a competitive fashion, either to the antibody or to the polypeptide partner. Catalytic activity is provided when the polypeptide labeled analyte binds to its polypeptide partner, but catalytic activity is inhibited, (i.e., not expressed or recovered) when the polypeptide labeled analyte binds the antibody.

Due to the equilibrating reactions of the system, and by the law of mass action, analyte displaces polypeptide labeled analyte bound to the antibody; and, as a result, there is available in the sample, unbound labeled analyte which is capable of binding with its polypeptide partner. Thus, in the absence of analyte, reduced catalytic activity is expressed. However, where analyte is present in the sample, increased catalytic activity occurs which can be monitored readily by the use of the substrates of this invention. Since catalytic activity will be diminished or inhibited when the labeled analyte is bound to the antibody, but will be recovered in the presence of analyte, the catalytic activity of the solution which is monitored by the substrate will be directly related to the concentration of analyte present in the sample.

In accordance with the present invention, the novel substrates have the following formula:

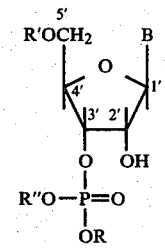

wherein:

B is a nucleotide base capable of assisting in hydrolysis of the phosphate ester at the 3'-position;

R is a moiety selected from the group consisting of umbelliferonyl, 4-methylumbelliferonyl, 3-flavonyl, o-nitrophenyl, m-nitrophenyl, p-nitrophenyl, dinitrophenyl, cyanophenyl, acylphenyl, carboxyphenyl, phenylsulfonate, phenylsulfonyl, and phenylsulfoxide;

R' is a moiety selected from the group consisting of hydrogen, alkyl, alkenyl, cycloalkyl, aryl, araalkyl, acyl, oxaalkyl, thioalkyl, oxacycloalkyl and thiocycloalkyl;

R" is hydrogen or a cation selected from the group consisting of calcium, barium, lithium, sodium, ammonium, substituted ammonium, or pyridinium.

Further, and importantly, there appear to be certain steric constraints which must be met in order to provide a substrate suitable for monitoring the catalytic activity of ribonuclease A-induced hydrolysis. Thus, the trans, cis orientation of the base B and substituents at positions 1' and 2', 3', respectively, appear to have rigid structural constraints to provide a suitable substrate. However, the substituents at the 4' position, that is, CH$_2$OR', may apparently have a configuration where the CH$_2$OR' group is cis to both the 2' and 3' functional groups, without affecting the desirable attributes of the substrate, A. Holy and F. Sorn, *Biochemica. Biophysica. Acta.*, 161, 264 (1968).

The base B assists in some fashion in the enzyme- or catalytic-induced hydrolysis of the phosphate ester at the 3'-position. This may occur by the base in effect, helping lock the substrate into an appropriate position in relation to the enzyme for hydrolysis. Further, the base may perhaps assist in the proton transfer involved in the hydrolysis.

Also, from the functional standpoint, the selection of the base should take into account the following factors in addition to, of course, its effect on product stability: (1) any modulation (increase or decrease) of enzymatic activity, (2) the difficulty of synthesis, (3) the effect on endogenous enzymatic activity and (4) the solubility in aqueous or other mediums of interest should not be adversely affected to any significant extent. Other factors to consider include possible effects on hydrolysis and non-specific medium induced hydrolysis.

A wide variety of pyrimidine analogs are useful including uracil, dihydrouracil, cytosine, dihydrocytosine and halogenated uracils. Additionally, based on data extrapolated from results on the ribonuclease-induced hydrolysis of both the natural substrate, RNA, as well as various synthetic substrates, such as, for example, nucleotide homopolymers, F. M. Richards and W. W. Wyckoff in *The Enzymes*, (P. D. Boyer, Ed.), *Academic Press*, 3d Edition, Volume 4, pages 647-806, London and New York (1978), the following pyrimidine analogs should be suitable bases:

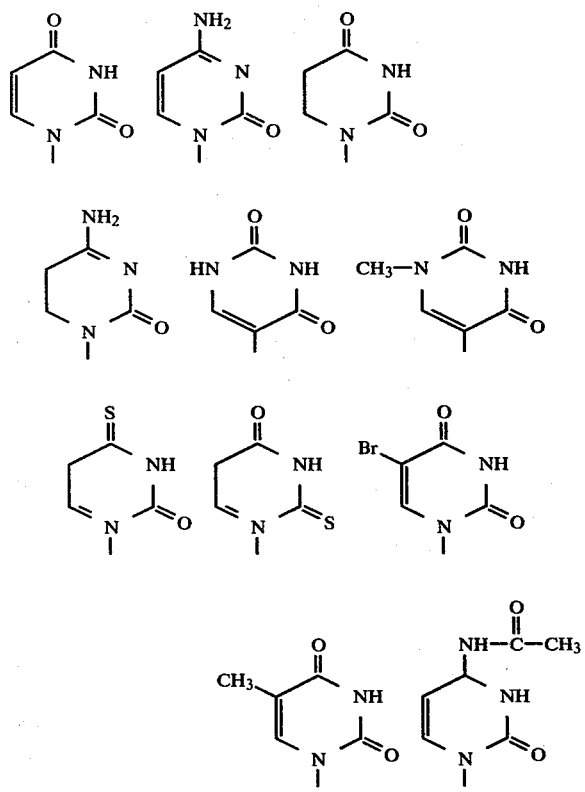

While the use of purine analogs as bases, such as, for example, adenosine and guanosine, will not provide active substrates for monitoring the catalytic activity of ribonuclease A, these bases should prove useful when ribonuclease T₂ activity is involved. Further, any other pyrimidine, purine or the like analogs may be used consistent with the functional considerations set forth herein.

The preferred group R is 4-methylumbelliferonyl, set forth below:

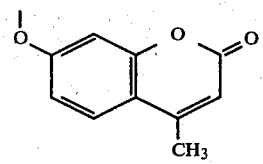

This group provides a substrate which can be utilized for both fluorometric and spectrophotometric immunoassays. Thus, this fluorophore has strong molar absorptivity, and as a consequence of the phenomenon known as the Weller cycle, A. Weller, *Prog. in Reaction Kinetics*, 1, 189 (1961), it has a distinct fluorescent emission in the alcohol form at long wavelength. The substrate absorbs at 315 nm and emits at 375 nm. On the other hand, the alcohol product from hydrolysis ionizes readily in the excited state and emission occurs from the excited anion. The excited anion, however, has a strong and efficient emission at 440-460 nm, which is far removed from the fluorescent emission of the substrate as well as from the fluorescent emission of other analyte sample components. Thus, the hydrolysis product 4-methylumbelliferone can be detected by a fluorescent excitation at 315 nm and monitoring emission at 460 nm at a pH as low as about 4 to 5. It has been found that as little as $5 \times 10^{-8}$ M of the fluorophore can be detected, substantially free of sample interferences.

The use of 4-methylumbelliferonyl as a colorimetric reporter group is based on the distinct absorbance which arises from the alcohol hydrolysis product also as a consequence of ionization to form the oxide. The unionized alcohol for the 4-methylumbelliferonyl group in the substrate absorbs with a maximum at about a wavelength of 315 nm. The oxide anion, however, has a maximum at a wavelength of 360 nm. The ground state alcohol is a relatively weaker acid so that the assay medium should be maintained at about a pH of about 6 to 8 in order to detect the unique absorbance of the anion. The use of a pH of higher than about 8, on the other hand, causes rapid medium-induced hydrolysis of the substrate and thus should be avoided.

Another useful chromophore/fluorophore R group is 3-flavonyl. The hydrolysis product alcohol has a unique intense fluorescent emission which can be readily detected. However, for this molecule, the fluorescent signal is markedly enhanced by chelation with aluminum$^{(+3)}$ ions. It has been found that a solution of 3-hydroxy flavone and aluminum$^{(+3)}$ ions has a fluorescence which is twenty times more intense than the fluorescence from an equimolar solution of 4-methylumbelliferone. The structure for the 3-hydroxyl flavone and the aluminum-chelated molecule thereof are shown below:

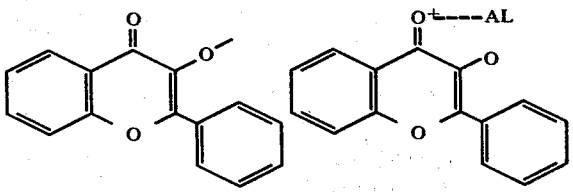

Many ionized aromatic alcohols have markedly different absorbances from that of the unionized alcohol. This situation prevails for many aromatic alcohols which contain electron withdrawing groups such as nitro, acyl or carboxyl; and these could be employed in the substrate for a spectrophotometric detection mode if the absorbance is also markedly different from that of the substrate as well. However, such materials may or may not have efficient emission, i.e.—a quantum yield of about 0.4 or more. Umbelliferone itself meets both the absorbance and fluorescent emission requirements and may be employed for the R group as well as any other substituted compounds of the other useful R groups identified herein, or, indeed, any other compounds which likewise meet such requirements. Further, other R groups which are suitable when only a chromophore is required are aryl groups which incorporate electron withdrawing and conjugating substituents which increase the acidity of ortho and para benzoic acids or phenols. Such groups include, ortho, meta and para nitrophenyl dinitrophenyl, cyanophenyl, acylphenyl, carboxyphenyl, phenylsulfonate, phenylsulfonyl, and phenylsulfoxide. In general, mixtures of mono and di-substituted derivatives may likewise be suitable.

As may be perhaps appreciated from the recitation of the useful R' groups in the structural formula for the substrate, a wide variety of groups may suitably be employed. The selection of the particular group for use should take into account the following functional considerations: (1) the solubility in aqueous or other mediums of interest should not be adversely affected to any significant extent, (2) the difficulty of synthesis, (3) the effect on endogenous enzymatic activity, (4) any modulation (increase or decrease) of enzymatic activity, and (5) the effect on hydrolysis and non-specific medium induced hydrolysis. Stated another way, the selection of the particular R' group will be principally dictated by the ease of synthesis so long as the particular group will not adversely effect the performance of the substrate in the intended assay. Modest changes in the rate of hydrolysis have been observed for various R' groups, and this may effect substrate performance, R. Kole, H. Sierakowska, D. Shugar, *Biochem. Biophys. Acta.*, 289, 323 (1972). This can be determined through usage. It has been found useful to use acetyl as R'.

Similarly, there are no stringent requirements for the R'' group; and its choice will be dictated by synthetic requirements, especially with respect to isolation and purification of the substrate product. As in the case of R', any selection may be made for R'' which does not adversely effect the performance of the substrate in the intended assay.

The substrate of this invention can undergo, in certain environments, medium-induced hydrolysis and this provides undesirable background conversion of the substrate to reporter molecule. This medium-induced hydrolysis reaction can occur with an umbelliferone moiety rapidly at high pH, i.e.—about 8 or more, but only very slowly at a lower pH. This may be of concern when long term storage (i.e.—more than one day or so) of these substrates is contemplated. Storage at a low pH and at relatively low temperatures will minimize hydrolysis.

However, in accordance with one aspect of this invention, it has been found that medium-induced hydrolysis can be essentially eliminated by derivatizing the 2' substitutent with an easily removable blocking group. To this end, the preferred composition, when long term storage is contemplated, is represented by the following formula:

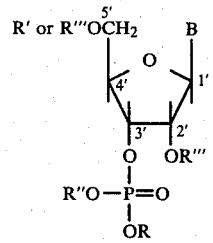

wherein:
R''' is a blocking group; and
R, R', R'' and B are the same moieties as described in conjunction with the previous formula for the novel substrates of this invention.

Suitable 2'-blocking groups should meet the following criteria: (1) readily introduced without affecting the other key functionalities, (2) compatible with subsequent synthetic steps, and more particularly, should minimize or eliminate undesired side reactions in such steps, (3) sufficiently stable to allow long-term storage without any adverse deleterious affects and (4) easily removed without disruption of the phosphodiester bond. These criteria, and especially the last one, are most readily met by use of a blocking group capable of being introduced and removed by acid-catalyzed reactions or certain nucleophilic reactions.

Thus, suitable blocking groups R''' include silyl, oxaalkyl, thioalkyl, oxacycloalkyl and thioalkyl. More particularly, tetrahydropyranyl, 4-methoxytetrahydropyranyl, 1-ethoxyethyl, t-butyldimethsilyl, triisopropylsilyl and t-butyltetramethylenesilyl may be used. Use of the first three blocking groups, that is, tetrahydropyranyl, 4-methoxytetrahydropyranyl, and 1-ethoxyethyl, lead to a ketal structure. These blocking groups are easily removed by weak acids, such as, for example, dilute hydrochloric acid or dilute acetic acid, without disruption of other key functional groups in the substrate molecule. The silyl blocking group is, likewise, easily removed by a nucleophilic reagent such as, for example, tetrabutylammonium fluoride.

The R''' blocking groups may be inserted at the 2' position on the furanoside ring in the course of the synthesis of the substrate itself. However, while not believed essential for providing satisfactory long term storage characteristics, blocking at the 5'-position is necessary during synthesis. Blocking at the 2'- and 5'-positions during synthesis thus prevents premature hydrolysis of synthetic intermediates as well as the occurrence of undesirable reactions at the 2'- and 5'-positions. The blocking group at the 5'-position need not be removed prior to use of the substrate so the requirement of being capable of being easily removed as is the case with the blocking of the 2'-position is not present.

One method for making the substrates of this invention involves as a specific illustration, the synthesis of 2'-O-tetrahydropyranyl-5'-O-acetyl-uridylic acid as an intermediate which is subsequently condensed with the free alcoholic fluorophore or chromophore to form a substrate within the generic formula set forth above. The synthetic steps are set forth schematically as follows, the R group being defined as previously discussed:

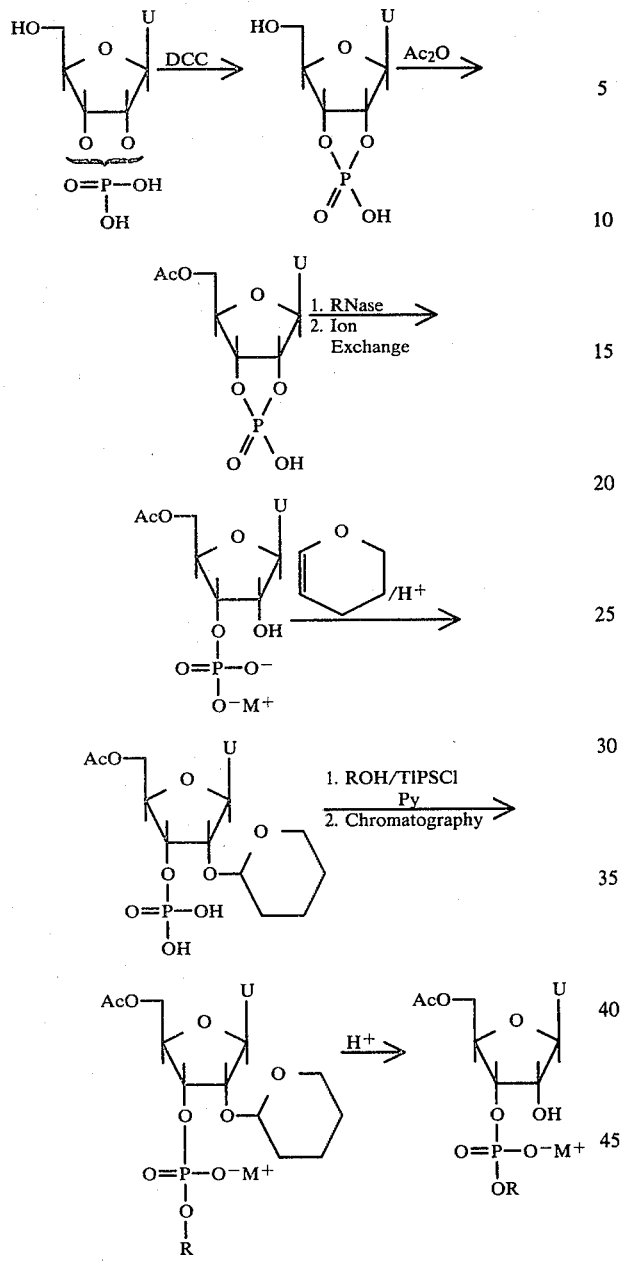

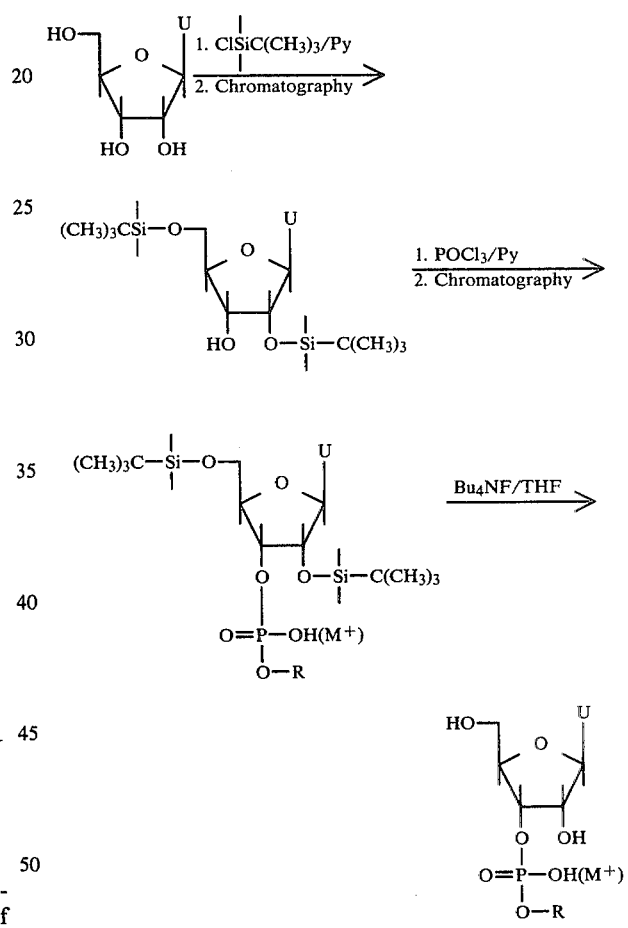

tration of the deblocking reagent and the temperature at which the deblocking reaction is carried out. Generally, the higher the temperature and the higher the concentration of acid, the shorter will be the appropriate reaction period. Thus, the reaction may be carried out for from about 5 minutes to about 24 hours. The use of too severe reaction conditions should be avoided as this may lead to deleterious hydrolysis of the deblocked substrate.

A second method for making the substrates of the present invention involves, as one specific example, the use of tert-butyldimethylsilyl blocking groups and is based on the direct silylation of uridine to form 2',5'-di(-tert-butyldimethylsilyl)-blocked uridine. This synthesis is set forth schematically as follows:

As can be seen, this method utilizes a 5'-acetyl substituent to eliminate the potential for the occurrence of diastereomeric pairs. The presence of the 5'-acetyl in the final substrate does not appreciably affect the catalytic-induced hydrolysis of the substrate as has been previously discussed herein. The chromatography step indicated in the above scheme for purification of the blocked phosphate diester species need not be carried out. After deblocking at the 2'-position, the product obtained has sufficient purity to allow usage in assays without purification.

Acid-catalyzed deblocking of the phosphate diester may be carried out in a protic solvent such as water using mild conditions with dilute acid for a short period of time. For example, dilute hydrochloric in a molar concentration of 0.01 to 0.05 at ambient temperatures is suitable. The deblocking reaction time may be varied over a relatively wide period, depending on the concen- The deblocking reaction is generally carried out, for example, using a 1 M solution of tetrabutylammonium fluoride in tetrahydrofuran at a temperature of about 15° C. to about 30° C. for a period of from about 20 minutes to about 30 minutes.

The following Examples are merely illustrative of the present invention and are not intended as a limitation on the scope thereof. Briefly, Examples I–XII are directed, generally, to the preparation of substrates coming within the generic formula of the substrates of this invention. Examples I–X and Examples XI and XII, set forth below are the same, respectively, as Examples I–X set forth in the co-pending Kang et al. application and Examples I and IV set forth in the co-pending Kang application, both previously identified. Examples XIII–

-XV show, generally, the use of substrates coming within the generic formula of the substrates of this invention in immunoassays. Examples XIII, XIV and XV set forth herein, are essentially the same as Examples XVII, XX and XXI, respectively, set forth in the previously identified co-pending Farina et al. application.

EXAMPLE I

This Example illustrates the preparation of uridine 2',3'-cyclic phosphate.

A solution of 10 g, 0.031 mole, comprising a mixture of uridine 2'- and 3'-phosphates in 74 ml of 3 N-ammonia was successively mixed with 60 ml of N,N-dimethylformamide (DMF), and a solution of 15 g, 0.075 mole, of dicyclohexylcarbodiimide in 60 ml of tert-butyl alcohol. The resulting reaction mixture was refluxed for three hours in an oil bath at 120° C.

A high pressure liquid chromotography (HPLC) analysis was done on a portion of the reaction mixture to determine whether the starting materials were converted to product. Aliquots of the reaction product mixture were concentrated under vacuum (bath 35° C.), dissolving the residue in water, and filtering the solution through a 5 μm Millipore ® filter. Samples were then injected into a Whatman Partisil ® 10/25 SAC column and eluted with buffer composed of 20% phosphate, 0.05 M at about pH 6.25, and 80% water at a flow rate of 1 ml/min. The HPLC analysis showed a quantitative conversion of starting uridine into product.

The total product mixture was then allowed to cool to room temperature, and dicyclohexylurea precipate was separated by filtration and washed with 20 ml of DMF. The filtrate was then evaporated in vacuo at 12–15 Torr, bath at about 35° C., and the residue was shaken with 100 ml of water and filtered to remove dicyclohexylurea. The solid was washed further with 20 ml of water, and combined solutions were extracted twice with 150 ml of ether, and evaporated to dryness in vacuo, bath at about 35° C. The residue was co-evaporated with two 100 ml portions of pyridine, using a liquid nitrogen trap at 0.01 Torr to obtain a glassy product, uridine 2',3'-cyclic phosphate.

EXAMPLE II

This Example illustrates the preparation of 5'-O-acetyluridine 2',3'-cyclic phosphate.

The uridine 2',3'-cyclic phosphate, prepared in Example I was dissolved in 100 ml of anhydrous pyridine and 200 ml of acetic anhydride. The solution was kept in the dark at room temperature overnight. At this point an aliquot of the reaction product was analyzed by HPLC at the conditions given in Example I. The HPLC showed one major peak at 1.7 minutes, which is indicative of the product 5'-O-acetyluridine 2',3'-cyclic phosphate. The total product mixture was evaporated to dryness at 0.1–1 Torr bath at about 35° C., using a liquid nitrogen trap. The residue was co-evaporated with two 50 ml portions of pyridine to remove residual acetic anhydride, and then dissolved in 100 ml of 50% aqueous pyridine. After stirring for one hour at room temperature, the solution was evaporated to dryness at room temperature, at 0.05 Torr to obtain product, 5'-O-acetyluridine 2',3'-cyclic phosphate.

EXAMPLE III

This Example illustrates the preparation of the ammonium salt of 5'-O-acetyluridine 3'-phosphate.

The glassy product, 5'-O-acetyluridine 2',3'-cyclic phosphate prepared in Example II was dissolved in 200 ml of 20% aqueous pyridine. To the solution was added 50 mg of pancreatic ribonuclease in 5 ml of water. The mixture was kept at room temperature overnight for approximately 15 hours with stirring in the dark. At this point, an aliquot of the reaction product was analyzed by HPLC at the conditions given in Example I. The HPLC showed one major peak at 4.5 minutes, which is indicative of the product 5'-O-acetyluridine-3'-phosphate. The product mixture was then passed through a 2.2×4 cm ion exchange resin column of Dowex ® 50W-X8, in which 100–200 mesh, hydrogen ion form resin had been converted to the pyridinium form before use. The resin was eluted with 300 ml of 20% aqueous pyridine. The eluant solution was concentrated to an oily residue at 0.1–1 Torr, bath at about 35° C. The oily residue was dissolved in 5 ml of water and 200 ml of tetrahydrofuran (THF). To the solution was added 27% NH$_4$OH dropwise with stirring until no more precipitate formed. Approximately 3 ml NH$_4$OH was added. The mixture was kept cold overnight, filtered, and washed successively with 50 ml of THF and 50 ml of acetone to collect product containing the ammonium salt of 5'-O-acetyluridine 3'-phosphate.

EXAMPLE IV

This Example illustrates the preparation of 5'-O-acetyl-2'-O(tetrahydropyran-2-yl) uridine 3'-ammonium phosphate.

A stirred suspension of 12 g, 0.026 mole, of the finely-ground ammonium salt of 5'-O-acetyluridine 3'-phosphate prepared in Example III, 160 ml of anhydrous N,N-dimethylformamide, and 70 ml of dihydropyran, was cooled to −20° C., and treated dropwise with 14.2 ml of 5 M hydrogen chloride in dioxane over a 15 minute period, under exclusion of atmospheric moisture. The cooling bath was then removed and stirring was continued until a clear solution was obtained, i.e., about two hours. After storage overnight at room temperature, the mixture was cooled to −20° C. and treated with 12 ml of triethylamine and 3 ml of ammonium hydroxide; and the resulting suspension was poured into 500 ml of THF and 500 ml of ether. The precipitate, collected on a medium porosity sintered-glass funnel, was washed with three 50 ml portions of ether, and air-dried. The solid was then triturated with 200 ml of chloroform, containing 0.1% triethylamine, and recollected with suction. This procedure was repeated with acetone, followed by acetone containing 0.1% triethylamine. After air drying first in air, and then at 0.01 Torr, the ammonium salt product was obtained.

EXAMPLE V

This Example illustrates the preparation of 5'-O-acetyl-2'-O-(tetrahydropyran-2-yl)uridine-3'-(4-methylumbelliferone-7-yl)ammonium phosphate.

A mixture comprising 1.00 g (2.01 mmole) of the 5'-O-acetyl-2'-O-(tetrahydropyran-2-yl)uridine ammonium phosphate prepared in Example IV and 0.531 g (3.00 mmole) of 4-methylumbelliferone and 1.52 g, (5.02 mmole) of 2,4,6-triisopropylbenzenesulfonyl chloride, in 6 ml of dry pyridine, was stirred under exclusion of atmospheric moisture. The mixture gradually became a homogeneous yellow solution after about 30 minutes at room temperature. After about one hour, the pyridine HCl salt precipitated. After stirring overnight, 6 ml of water were added and the stirring was continued for an additional two hours. The mixture was concentrated at room temperature, in vacuo, using a liquid nitrogen trap, and the solid product mixture was dissolved in 15 ml of water. The solution was extracted five times with 50 ml ether, per extraction, until most of the unreacted 4-methylumbelliferone was removed, as indicated by the decrease in fluorescent emission at 450 nm when the solution was excited at 325 nm. The water solution was lyophilized, in vacuo, to give product containing 5'-O-acetyl-2'-O-(tetrahydropyran-2-yl)uridine-3'-(4-methylumbelliferone-7-yl)ammonium phosphate.

EXAMPLE VI

This Example illustrates the preparation of 5'-O-acetyluridine-3'-(4-methylumbelliferone-7-yl)ammonium phosphate.

Prior to use, the product containing 5'-O-acetyl-2'-O-(tetrahydropyran-2-yl)uridine-3'-(4-methylumbelliferone-7-yl)ammonium phosphate prepared in Example V was readily deblocked with hydrochloric acid. Fifteen milligrams of the product containing 2',5'-diblocked phosphodiester were added to 1 ml of 0.01 N HCl to give a clear solution. After 45 minutes, the product solution was extracted six times with 1 ml of ether to remove residual 4-methylumbelliferone. Nitrogen was then blown across the aqueous solution to remove the last traces of ether. The working solution was prepared by diluting to 100 ml with 0.1 N sodium acetate buffer of about pH 5.0. The substrate was stable in the working buffer for at least two days at 4° C.

EXAMPLE VII

This Example illustrates the preparation of the calcium salt of 5'-O-acetyluridine 3'-phosphate.

The 5'-O-acetyluridine 2',3'-cyclic phosphate prepared as described in Examples I and II (from using 4 grams of a mixture of the 2'- and 3'-phosphate isomers of uridine) was dissolved in 100 ml of 20% aqueous pyridine. To the solution there was added 50 mg of pancreatic ribonuclease A. The solution was strred in the dark at room temperature for 15 hours.

An aliquot of the solution was analyzed, after removal of ribonuclease A by passing through Dowex ®-50 column, by HPLC at the conditions given in Example I. The analysis showed a very small amount of starting cyclic phosphate at 1.7 minutes and a major product peak at 4.5 minutes.

An additional 20 mg of ribonuclease A was added to the remaining product mixture and the mixture was allowed to stir at room temperature for an additional 3 hours. The product solution was passed through a Dowex ®-50 (1×5 cm) column by eluting with 160 ml of 20% aqueous pyridine. The solution was concentrated to about 50 ml and poured into 1000 ml of anhydrous ethanol containing 5 g of calcium chloride. The mixture was stirred at room temperature for 2 hours and then allowed to stand to precipitate the calcium salt. The precipitate was collected by centrifugation at 3000 rpm for about 5 to 10 minutes, and repeated washing (7×150 ml) with ethanol and centrifugation.

The calcium salt cake was washed with two 150 ml portions of ether and dried in air. After drying further in vacuo, there was obtained 13.1 g of product containing calcium salt of 5'-O-acetyluridine 3'-phosphate as confirmed by HPLC analysis (at the conditions given above) which showed one major product peak at 4.5 minutes.

EXAMPLE VIII

This Example illustrates the preparation of 5'-O-acetyl-2'-O-(4-methoxytetrahydropyran-4-yl)uridine-3'-calcium phosphate, utilizing 5,6-dihydro-4-methoxy-2H-pyran as a 2'-blocking reagent.

One gram of 5'-O-acetyluridine 3'-calcium phosphate prepared in Example VII was dissolved in 8 ml of dry N,N-dimethylformamide. To this solution was added 5.0 g of 5,6-dihydro-4-methoxy-2H-pyran. The solution was cooled in an acetone-ice bath to below 0° C. To the stirred mixture there were added 1.4 ml of 5 M hydrogen chloride in N,N-dimethylformamide dropwise in a moisture excluded atmosphere. After about 20 minutes, the cooling bath was removed; and the reaction mixture was stirred at room temperature overnight, about 15 hours. This mixture was again cooled in an acetone-ice bath, and 25 ml of triethylamine was added dropwise with stirring. The product mixture was poured into 100 ml of ether and filtered to collect white powder. The powder was washed with 100 ml of ether, and with 100 ml of 1% triethylamine in chloroform.

The solid was first air dried and then further dried in vacuo to give 1.398 g of product containing 5'-O-acetyl-2'-O-(4-methoxytetrahydropyran-4-yl)uridine-3'-calcium phophsate.

HPLC on Whatman Partisil ® PXS 10/25 SAX column eluting with 0.01 M phosphate buffer, pH 6.3, flow rate 1 ml/min., UV detection at 253 nm, showed product at 3.4 min., while the starting materal has retention time of 4.7 minutes.

EXAMPLE IX

This Example illustrates the preparation of 5'-O-acetyl-2'-O-(4-methoxytetrahydropyran-4-yl)uridine-3'-(4-methylumbelliferone-7-yl) phosphate.

The hydrogen ion form of Bio-Rad AG ® 50W-X8 cation exchange resin, 1.1 g, was converted into the pyridinium form. To the column there was added 100 mg of the product containing 5'-O-acetyl-2'-O-(4-methoxytetrahydropyran-4-yl)uridine 3'-calcium phosphate prepared in Example VIII, dissolved in cold 50% pyridine solution, and the column was eluted with 270 ml of 50% pyridine solution. The eluant solution was collected in a flask cooled in an ice-water bath. The eluant solution was concentrated to 15 ml on a rotary evaporator using a dry ice trap at bath temperature of about 25° C. The remaining solution was further concentrated in vacuo using a liquid nitrogen trap (0.05 Torr) at room temperature to obtain a glassy residue. The residue was further dried by evaporating twice with dry pyridine.

Finally, the residue was dissolved in 1 ml of dry pyridine; and the mixture was charged with 52.72 mg of 4-methylumbelliferone and 102.7 mg of 2,4,6-triisopropylbenzenesulfonyl chloride. The mixture was cooled in an ice-water bath with stirring for 15 minutes. The resulting yellow solution was further stirred at room temperature for 2 hours and allowed to stir overnight, that is, about 15 hours at about 4° to 8° C. The total product mixture was then stirred with 3 ml of a saturated solution of tetraethylammonium bromide for 5 minutes, and then extracted five times with chloroform. The chloroform layer was concentrated in vacuo to yield 635 mg of light gray solid crude product.

The phosphodiester was further purified by an anion exchange column chromatography eluted with ammonium bicarbonate buffer. The appropriate fractions were identified by assay with RNase after deblocking in the manner given in Example VI. The fractions so identified were pooled and concentrated to give 137 mg of solid, which was then dissolved in methanol and evaporated repeatedly in vacuo to remove ammonium bicarbonate. As a result, 59 mg of product containing 5'-O-acetyl-2'-O-(4-methoxytetrahydropyran-4-yl)uridine 3'-(4-methyllumbelliferone-7-yl) phosphate were obtained.

EXAMPLE X

This Example illustrates the preparation of 5'-O-acetyl-2'-O-(4-methoxytetrahydropyran-4-y)-uridine-3'-flavonyl phosphate.

Fifty milligrams of the product containing 2'-O-(4-methoxytetrahydropyran-4-yl)-5'-O-acetyl-3'-uridine calcium phosphate prepared in Example VIII, was converted into the pyridinium salt by passing it through a pyridinium form of Bio-Rad AG ® 50W-X8, cation exchange column. The pyridine solution was concentrated in vacuo and further dried by repeated evaporation with dry pyridine to obtain a glassy residue.

The glassy residue was dissolved in 1 ml of dry pyridine, and the solution was charged with 35.6 mg of 3-hydroxyflavone and 51.4 mg of 2,4,6-triisopropylbenzenesulfonyl chloride, with stirring in an ice-water bath under nitrogen atmosphere. After 15 minutes, the mixture was allowed to warm up to room temperature and stirred over the weekend, about 3 days.

The reaction mixture was then monitored for product formation. A 0.3 ml aliquot of the reaction mixture was stirred with 1 ml of saturated tetraethylammonium bromide and extracted with chloroform 4 times. The chloroform was evaporated, and the resulting yellow solid was treated with 0.01 N HCl for 40 minutes. The solution was then buffered at pH 5 with a 0.1 M acetate buffer containing $4 \times 10^{-3}$ M aluminum chloride and 1% dimethylsulfoxide. The resulting buffered solution, in the presence of RNase enzyme, produced fluorescent emission characteristics of aluminum chelated 3-hydroxyflavone, thereby indicating that the desired product had formed.

The remainder of the reaction mixture was stirred for 5 minutes with 2 ml of a saturated solution of tetraethylammonium bromide. The mixture was then extracted four times with chloroform. The chloroform layer was dried over anhydrous sodium sulfate and concentrated to give 0.355 g of yellow solid product. The product was further purified by chromatography on a silica gel column, 2.5×6.5 cm, and eluted with 10% methanol in chloroform. Fractions of 100 milliliters each were collected and fractions 9, 10 and 11 were shown to have positive substrate activity when deblocked in acid, and assayed with RNase.

The fractions 9, 10 and 11 were combined and concentrated to obtain 160 mg of product containing 5'-O-acetyl-2'-O-(4-methoxytetrahydropyran-4-yl)uridine 3'-flavonyl phosphate.

EXAMPLE XI

This Example illustrates the preparation of 2',5'-bis-t-butyldimethylsilyluridine.

In the preparation of 2',5'-bis-t-butyldimethylsilyluridine, 11.39 g, 0.0466 mole, of uridine was dissolved in 80 ml of pyridine by stirring at room temperature for about 5 min. Then 21.09 g, 0.140 mole, t-butyldimethylsilyl chloride was added to the pyridine solution and the mixture was stirred at room temperature for about 62 hours in a flask fitted with a drying tube. The reaction mixture was diluted with 150 ml ether and then filtered to remove pyridine- HCl. The etherpyridine filtrate was concentrated on a rotary evaporator and then in high vacuum using a liquid nitrogen trap.

Thin layer chromatography of an aliquot of the reaction product mixture on silica gel with a solvent of two parts of ether and one part, by volume hexane showed three components, respectively, at $R_f$ 0.65, 0.5 and 0.3.

The remainder of the oily reaction product mixture was chromatographed on a 4.2×44 cm silica gel column comprising Silica gel 60 (EM ® Reagent, Lot No. 7953179), of particle size 0.063–0.2 mm and 70–230 mesh (ASTM) with a solvent of two parts of hexane and one part ethyl acetate by volume, to separate the three components of the reaction product mixture. The fractions having $R_F$ of 0.5, identified by thin layer chromatography at the conditions given above, were combined. Additionally, fractions containing the $R_f$ 0.3 and 0.65 components were rechromatographed to isolate additional $R_f$ 0.5 product. All fractions found to contain the component having $R_f$ 0.5 were combined. The combined yield was 8.961 g, that is 40.5%. The melting point (123°–125° C.) and n.m.r. spectrum (CDCl$_3$) of the product confirmed the product as 2',5'-bis-t-butylmethylsilyluridine.

EXAMPLE XII

This Example illustrates the preparation of 2',5'-bis-tert-butyldimethylsilyl-3'-uridine (4-methylumbelliferone-7-yl)phosphate.

In this Example, 2',5'-bis-tert-butyldimethylsilyluridine is phosphorylated to form a reactive intermediate which is reacted with 4-methylumbelliferone.

In a round bottom flask, 0.2386 g of 2',5'-bis-tert-butyldimethylsilyluridine was dissolved in 5 ml of dry pyridine. The solution was evaporated to dryness in vacuo. The residue solid was redissolved in 7 ml of dry tetrahydrofuran and 4 ml of pyridine, and cooled with stirring in an ice-water bath under exclusion of atmospheric moisture. To the stirred cold solution there was added 0.5 ml of phosphorus oxychloride, using an air tight syringe. The mixture was allowed to stir for 5 minutes in a cooling bath, and then at room temperature for 1.5 hours. Pyridine HCl salt was deposited in the bottom of the flask.

An aliquot of the reaction mixture was analyzed by thin layer chromatography to monitor the formation of the intermediate. The chromatography was carried out on a silica gel plate with a solvent system comprising ethylacetate, chloroform and hexane in the ratio, by volume, of 5:2:3. The analysis showed a component with $R_f$ near the origin. However there was no component with $R_f$ 0.55 thereby indicating that the uridine starting material had been completely consumed.

The remainder of the reaction mixture was concentrated in vacuo using a liquid nitrogen trap to remove unreacted phosphorus oxychloride. To the residue there was added 0.107 g of 4-methylumbelliferone, and the mixture was cooled in an ice-water bath under nitrogen atmosphere to exclude atmospheric moisture. To the mixture, there was added 4 ml of dry pyridine; and the resulting solution was stirred at room temperature for 40 minutes.

An aliquot of the resulting light yellow solution was analyzed by thin layer chromatography, at the same conditions as given above. A new fluorescent spot, believed to be 2',5'-bis-tert-butyldimethylsilyl 3'-uridine-(4-methylumbelliferone-7-yl)phosphate, was found.

The remainder of the solution was concentrated in vacuo to a glassy oil. The oil was suspended in 5 ml of tetrahydrofuran (THF). To the THF suspension, there was added 20 ml of ether; and the mixture was stored in a cold room at about 4° to 8° C. to precipitate product. The product was collected by filtration and dried over $P_2O_5$ in vacuo to yield 0.572 g of light gray powder. The product as obtained in this fashion was confirmed by n.m.r. to contain 2',5'-bis-tert-butyldimethylsilyluridine 3'-(4-methylumbelliferone-7-yl)phosphate.

The 2',5'-bis-tert-butyldimethylsilyl-uridine-3'-(4-methylumbelliferone-7-yl)phosphate was deblocked following the same procedure as set forth in Example VI, to form 3'-uridine-(4-methylumbelliferone)phosphate, which was identified by enzyme assay. In an assay with RNase enzyme, the assay mixture was excited at 325 nm and monitored emission at 450 nm of the fluorogenic 4-methylumbelliferone, resulting from enzyme hydrolysis of 3'-uridine(4-methylumbelliferone-7-yl)phosphate.

EXAMPLE XIII

This Example illustrates the generation of a reference displacement curve using thyroxine-S peptide as the labeled analyte and 5'-O-acetyl uridine-3'-(4-methylumbelliferone-7-yl)phosphate as a fluorogenic substrate. The following reagents were prepared:

a. Thyroxine-S-Peptide labeled analyte: Material prepared in the manner described in Examples I–IV of co-pending Farina et al., was diluted by a factor of 1:2000 in 0.1 M sodium acetate buffer of pH 5.0.

b. Antibody: Antiserum was diluted by a factor of 1:2000 using 0.1 M sodium acetate buffer of pH 5.0;

c. S-Protein: Purified material was brought to $2 \times 10^{-5}$ M using 0.1 M sodium acetate buffer of pH 5.0;

d. Substrate: Seventeen milligrams of 5'-O-acetyl-2'-O-(tetrahydropyran-2-yl) uridine 3'-(4 methylumbelliferone-7-yl ammonium phosphate was stirred in 0.01 HCl for 45 minutes and then extracted with ether. Fifty ml of 0.01 M sodium acetate buffer, of pH 5, was then added to give the substrate solution;

e. Thyroxine antibody standards: Thyroxine solutions were freshly prepared to provide thyroxine concentrations of 0 ng/ml, 30 ng/ml, 60 ng/ml, 120 ng/ml, and 240 ng/ml in an aqueous medium containing human serum.

Seventy-five microliters of the standard thyroxine solution was pretreated with 20 ul of 0.5 N sodium hydroxide for 10 minutes at room temperature. One hundred microliters of the antibody and 300 ul of thyroxine-S-peptide labeled analyte solutions were then added, and the mixture was incubated for 30 minutes at room temperature. A mixture consisting of 1.8 ml of substrate and 100 ul S-protein was then added. After incubating for 5 minutes, the rate of increase of fluorescence was monitored over a 10 minute period.

An Aminco ® Filter Fluorometer (Model J4-7440) equipped with an automatic 20 sample changer (Model 047-67059) was utilized with excitation at 325 nm and emission at 440 nm. The data points were taken for each sample at times 0, 5, and 10 minutes by an automatic data acquisition system. Table 1 summarizes the results:

TABLE 1

| Tube | Antibody (ul) | Standard (ng/ml,ul) | Thyroxine-S peptide labeled analyte (ul) | Substrate/ protein (ml) | Rate (mv/min) |
|---|---|---|---|---|---|
| 1 | 175 (Buffer) | — | 300 | 1.8 | 15.14 |
| 2 | 175 (Buffer) | — | 300 | 1.8 | 14.76 |
| 3 | 100 | 0,75 | 300 | 1.8 | 12.48 |
| 4 | 100 | 0,75 | 300 | 1.8 | 12.44 |
| 5 | 100 | 30,75 | 300 | 1.8 | 13.00 |
| 6 | 100 | 30,75 | 300 | 1.8 | 13.57 |
| 7 | 100 | 60,75 | 300 | 1.8 | 13.30 |
| 8 | 100 | 60,75 | 300 | 1.8 | 13.40 |
| 9 | 100 | 120,75 | 300 | 1.8 | 13.68 |
| 10 | 100 | 120,75 | 300 | 1.8 | 13.68 |
| 11 | 100 | 240,75 | 300 | 1.8 | 14.15 |
| 12 | 100 | 240,75 | 300 | 1.8 | 14.17 |

The above data show that displacement of bound-labeled analyte occurs as the concentration of thyroxine analyte increases. In order to obtain a displacement curve, the data for duplicate points are averaged; and the % bound fraction (% $B/B_o$) is calculated from the equation:

$$B/B_o \times 100 = \frac{\text{Total Rate} - \text{Rate } B_n}{\text{Total Rate} - \text{Rate } B_o}$$

where Rate $B_n$ is the rate corresponding to a non-zero standard and Rate $B_o$ is that corresponding to the zero standard solution.

The results are shown in Table 2 below:

TABLE 2

| Point | Std. Conc (ng/ml) | Rate (mv/min) | % $B/B_o$ |
|---|---|---|---|
| Total | — | 14.95 | — |
| $B_o$ | 0 | 12.46 | 100 |
| $B_1$ | 30 | 13.28 | 67 |
| $B_2$ | 60 | 13.35 | 64 |
| $B_3$ | 120 | 13.68 | 51 |
| $B_4$ | 240 | 14.16 | 32 |

The above data can be used to construct a reference displacement curve where rate, % $B/B_o$, or the logit transformation is plotted as a function of standard concentration.

EXAMPLE XIV

This Example illustrates the generation of a reference displacement curve for the dilantin analyte on the CentrifiChem ® 500 centrifugal fast analyzer. A colorimetric substrate, 5'-O-acetyl-uridine-3'-(4-methylumbelliferone-7-yl phosphate), was used.

The following reagents were prepared:

a. Dilantin-S peptide labeled analyte: Material prepared in the manner described in Examples V–VII of co-pending Farina et al., in 0.1 M triethanolamine (TEA)-HCl buffer, was used.

b. Antibody: Anti-dilantin antisera was diluted by a factor of 1/20 with 0.1 M TEA-HCl buffer of pH 7.1;

c. Substrate: Seventeen milligrams of 5'-O-acetyl 2'-O-(tetrahydropyran-2-yl) uridine 3'-(4-methylumbelliferone-7-yl ammonium phosphate) was added to 750 ul 0.05 N HCl and stirred at room temperature for 30 min. Sodium acetate buffer, (1.880 ml, 0.1 M, pH 5.0), was added. Just before use, 300 ul of this solution was combined with 5.094 ml of 0.1 M TEA-HCl buffer of pH 7.1;
d. S-protein: Sigma purified commercial material was diluted by a factor of 1:100 with 0.1 M TEA-HCl buffer of pH 7.1 to give a solution having a concentration of $1.53 \times 10^{-6}$ M;
e. Dilantin standards: A stock solution of 5,5-diphenylhydantoin sodium salt (Sigma Lot 64C-0027) was made up by dissolving 48 mg in 1 liter of 0.025 N sodium hydroxide. This was diluted by a factor of 1:10 with 0.025 N sodium hydroxide to give a solution having 4.8 ug/ml. This was further diluted to give standard solutions having concentrations of 19.1, 47.8, 95.8, 143.6, and 191.5 ng/ml.

The CentrifiChem® 500 centrifugal fast analyzer had the following instrument settings: rotor temp, 30°; filter, 340 nm; $T_o$, 10 sec; T, 1 min; ABS 1.0 u; Blank, hold; test mode, Term; print out, ABS; conc. factor, 0; test code 0.

Antibody, dilantin-S-peptide and 16.6 ul of the standard solution were pipetted into the sample well of channels 3 to 16 of the transfer disc. S-protein and 300 ul of substrate were pipetted into each of the corresponding reagent wells of the transfer disc. The transfer disc was placed on the rotor and spun. Absorbance readings were measured at 1 min intervals for a period of 5 minutes and displayed by the CentrifiChem® data acquisition module. Catalytic activity rates (a.u./min) were obtained from a least squares regression analysis of absorbances as a function of time.

The data is summarized in Table 3 below:

TABLE 3

| Channel | Std. (ng/ml) | TEA—HCl Buffer (ul) | Antibody (ul) | Rate (a.u./min) |
|---|---|---|---|---|
| 3 | 0 (0.025N NaOH) | 33.3 | — | 0.0225 |
| 4 | 0 (0.025N NaOH) | 33.3 | — | 0.0230 |
| 5 | 0 (0.025N NaOH) | — | 33.3 | 0.0148 |
| 6 | 0 (0.025N NaOH) | — | 33.3 | 0.0145 |
| 7 | 19.1 | — | 33.3 | 0.0154 |
| 8 | 19.1 | — | 33.3 | 0.0171 |
| 9 | 47.8 | — | 33.3 | 0.0183 |
| 10 | 47.8 | — | 33.3 | 0.0158 |
| 11 | 95.8 | — | 33.3 | 0.0191 |
| 12 | 95.8 | — | 33.3 | 0.0197 |
| 13 | 143.6 | — | 33.3 | 0.0204 |
| 14 | 143.6 | — | 33.3 | 0.0180 |
| 15 | 191.5 | — | 33.3 | 0.0209 |
| 16 | 191.5 | — | 33.3 | 0.0205 |

EXAMPLE XV

This Example illustrates the design of an assay capable of directly assaying clinical samples, the use of the automatic pipetter (Model P-500) associated with the Centrifichem® 500 centrifugal fast analyzer, and the use of automatic data reduction.

The following reagents were utilized:
a. Labeled Analyte: Dilantin-S-peptide labeled analyte prepared in the manner described in Examples V–VIII of co-pending Farina et al., in 0.1 M triethanolamine (TEA)-HCL buffer, was used.
b. Antibody: Anti-dilantin antiserum (150 ul) was diluted with 900 ul of 0.1 M TEA-HCL buffer of pH 7.1;
c. Substrate: 5'-O-acetyl 2'-O-(tetrahydropyran-2-yl)uridine 3'-(4-methylumbelliferone-7-yl) ammonium phosphate (6.4 mg) was added to 285.2 ul of 0.05 N HCl and stirred at room temperature for 30 minutes. Sodium acetate buffer (714.8 ul, 0.1 M, pH 5.0) was then added;
d. S-protein: A $12.3 \times 10^{-5}$ M solution of Sigma S-protein was made up in 0.1 M TEA-HCl buffer (pH 7.1);
e. Dilantin standards: Solutions of 5,5-diphenylhydantoin sodium salt (Sigma lot 64C-0027) were made up in human serum at concentrations of 2.5, 5.0, 10.0, 20.0 and 30.0 ug/ml.

A mixture of 16 ul S-peptide labeled analyte, 10 ul of human serum albumin, 1430 ul of TEA-HCl buffer, and the substrate solution described in (c.) was prepared (designated Reagent 1). A second mixture consisting of 150 ul of antiserum, 50 ul of S-protein, and 1937.5 ul of TEA buffer was prepared (designated Reagent 2). Using the CentrifiChem® P-500 automatic pipetter, 4 ul of the appropriate standard solution was simultaneously diluted with 45 ul of deionized H$_2$O and pipetted into the sample well of transfer disc. At the same time, the pipetter delivered 250 ul of Reagent 1 into the reagent well and 100 ul of Reagent 2 into the sample well. Instrumental parameters for the CentrifiChem® 500 centrifugal fast analyzer were the same as that for Example XIV with the exception that Test Code 29 was used. This provides for automatic data reduction by the microprocessor unit of the CentrifiChem® 500 instrument.

The following data was obtained:

TABLE 4

| Standard Conc. (ug/ml) | $10^3$ Response (a.u.) | Calc. Standard Conc. (ug/ml) |
|---|---|---|
| 0 | 215 | 0 |
| 0 | 218 | 0 |
| 2.5 | 230 | 3.1 |
| 2.5 | 231 | 3.3 |
| 5 | 252 | 5.0 |
| 5 | 256 | 5.2 |
| 10 | 358 | 9.6 |
| 10 | 373 | 10.2 |
| 20 | 512 | 23.0 |
| 20 | 494 | 19.1 |
| 30 | 525 | 28.5 |
| 30 | 524 | 27.9 |

The logit-log standard curve stored in the microprocessor unit had a percentage standard deviation of 7.4. In general, the calculated standard concentrations derived from the stored curve satisfactorily agreed with the actual standard concentrations over the analyte concentration range as shown in Table 4.

The above protocol could be used for the direct assay of both control and clinical samples. For example, a clinical sample having a dilantin concentration of 23.4 ug/ml on the basis of gas liquid chromatographic (glc) determination was found to have a concentration of 23.3±0.7 ug/ml by duplicate assay as above. Similarly, a clinical sample having a concentration of 2.0 ug/ml by glc was found to have a concentration of 3.1±0.1 ug/ml. This illustrates good accuracy and sensitivity over the anticipated analyte range of concentrations in clinical samples. Furthermore, the data indicates the suitability of the assay for automatic pipetting and data reduction and thus takes advantage of the full capability of the centrifugal fast analyzer system utilized. Finally, the data demonstrates the adjustment of concentrations of antibody, S-protein, and dilantin-S-protein labeled analyte to allow for direct determination of clinical samples without prior dilution, beyond that carried out automatically by the P-500 pipetter.

What is claimed is:

1. A substrate having the following structural formula:

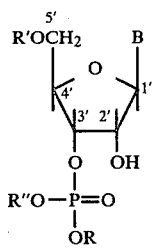

wherein B is a nucleotide base capable of assisting in hydrolysis of the phosphate ester at the 3'-position, R is a moiety selected from the group consisting of umbelliferonyl, 4-methyl umbelliferonyl, 3-flavonyl, o-nitrophenyl, m-nitrophenyl, p-nitrophenyl, dinitrophenyl, cyanophenyl, acylphenyl, carboxyphenyl, phenylsulfonate, phenylsulfonyl and phenylsulfoxide, R' is a moiety selected from the group consisting of hydrogen, alkyl, alkenyl cycloalkyl, aryl, araalkyl, acyl, oxaalkyl, thioalkyl, oxacycloalkyl, and thiocycloalkyl, and R" is hydrogen or a cation selected from the group consisting of calcium, barium, lithium, sodium, ammonium, substituted ammonium and pyridinium, said substrate being capable of undergoing enzymatic-induced hydrolysis of the phosphate ester at the 3'-position to yield a species capable of being monitored spectrophotometrically or fluorometrically.

2. The substrate of claim 1 wherein B is a pyrimidine analog.

3. The substrate of claim 2 wherein B is a member selected from the group consisting of uracil, dihydrouracil, cytosine, dihydrocytosine and halogenated uracils.

4. The substrate of claim 2 wherein B is a uracil.

5. The substrate of claim 1 wherein R is umbelliferonyl.

6. The substrate of claim 1 wherein R is 4-methyl umbelliferonyl.

7. The substrate of claim 1 wherein R is flavonyl.

8. The substrate of claim 1 wherein R' is acetyl.

9. The substrate of claim 1 wherein R" is calcium.

10. The substrate of claim 1 wherein R" is a member selected from the group consisting of ammonium, or substituted ammonium.

11. A substrate at least essentially stable towards medium-induced hydrolysis of the phosphate ester at the 3'-position and having the following structural formula:

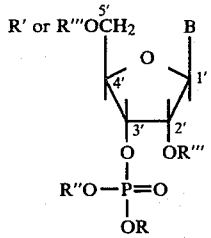

wherein B is a nucleotide base capable of assisting, after deblocking of the substrate, in hydrolysis of the phosphate ester at the 3'-position, R is a moiety selected from the group consisting of umbelliferonyl, 4-methyl umbelliferonyl, 3-flavonyl, o-nitrophenyl, m-nitrophenyl, p-nitrophenyl, dinitrophenyl, cyanophenyl, acylphenyl, carboxyphenyl, phenylsulfonate, phenylsulfonyl and phenylsulfoxide, R' is a moiety selected from the group consisting of hydrogen, alkyl, cycloalkyl, aryl, araalkyl, acyl, oxaalkyl and oxacycloalkyl, and R" is hydrogen or a cation selected from the group consisting of calcium, barium, lithium, sodium, ammonium, substituted ammonium and pyridinium and R''' is a blocking group capable of at least essentially preventing medium-induced hydrolysis of the phosphate ester at the 3' position, R''' being capable of being removed to provide a substrate characterized by the ability to undergo catalytic induced hydrolysis of the phosphate ester at the 3' position to yield a species capable of being monitored spectrophotometrically or fluorometrically.

12. The substrate of claim 11 wherein the moiety at the 5' position is R'''.

13. The substrate of claim 12 wherein R''' is a member selected from the group consisting of tetrahydropyranyl, 4-methoxytetrahydropyranyl, 1-ethoxyethyl and t-butyl dimethylsilyl.

14. The substrate of claim 13 wherein R''' is t-butyl dimethylsilyl.

15. The substrate of claim 11 wherein R' is acetyl and R''' is tetrahydropyran-2-yl.

* * * * *